(12) United States Patent
Cegla

(10) Patent No.: US 8,267,090 B2
(45) Date of Patent: Sep. 18, 2012

(54) THERAPEUTIC DEVICE

(75) Inventor: Ulrich Hartmann Cegla, Montabaur (DE)

(73) Assignee: R. Cegla GmbH & Co. KG, Montabaur (DE)

( * ) Notice: Subject to any disclaimer, the term of this patent is extended or adjusted under 35 U.S.C. 154(b) by 686 days.

(21) Appl. No.: 12/322,165

(22) Filed: Jan. 29, 2009

(65) Prior Publication Data

US 2009/0199853 A1 Aug. 13, 2009

(30) Foreign Application Priority Data

Feb. 8, 2008 (DE) .................. 10 2008 008 161

(51) Int. Cl.
*A61M 16/00* (2006.01)
*A62B 9/06* (2006.01)

(52) U.S. Cl. ......... 128/207.14; 128/200.24; 128/203.12; 128/207.15; 128/207.16; 128/207.17

(58) Field of Classification Search ............ 128/203.12, 128/207.14, 207.15, 207.16, 200.24
See application file for complete search history.

(56) References Cited

U.S. PATENT DOCUMENTS

| 4,966,141 A * | 10/1990 | Bacaner et al. .......... 128/207.14 |
| 5,329,921 A * | 7/1994 | Socaris et al. ........... 128/207.14 |
| 5,569,122 A * | 10/1996 | Cegla .............................. 482/13 |
| 6,729,334 B1 * | 5/2004 | Baran ...................... 128/207.14 |
| 7,900,625 B2 * | 3/2011 | Kleinstreuer et al. ... 128/203.23 |

FOREIGN PATENT DOCUMENTS

| EP | 0 681 853 | 11/1995 |
| EP | 1 772 165 | 4/2007 |

* cited by examiner

*Primary Examiner* — Lynne Anderson
*Assistant Examiner* — Bradley Philips
(74) *Attorney, Agent, or Firm* — Pandiscio & Pandiscio

(57) ABSTRACT

A therapeutic device for improving the respiration of a patient, with a curved or bent pipe section and a mouthpiece inserted in a first end of the mouthpiece and adapted to provide an easy-to-handle medicinal device by means of which diseases of the airway can be treated, or the pulmonary volume, as well as the pulmonary inhalation performance, of a patient can be improved. This is achieved in that a holding peg connected to the pipe section can be pushed into a second end of the pipe section, and a passage channel disposed in the holding peg which penetrates into the inside of the pipe section, completely or in part, and the holding peg has a flexible hose is attached to it which runs inside the pipe section, the free end of which can move freely in the area of the mouthpiece between inner walls of the pipe section.

12 Claims, 6 Drawing Sheets

THERAPEUTIC DEVICE

BACKGROUND OF THE INVENTION

1. Field of the Invention

The present invention relates to a therapeutic device for improving the respiration of a patient, with a curved or bent pipe section and a mouthpiece inserted in its first end.

2. Description of the Prior Art

A therapeutic device for supporting the respiration of a patient is disclosed in EP 0681853. In this case, the curved pipe section has a height-adjustable mouthpiece inserted in its end. As a result, the mouthpiece penetrates inside the pipe section in areas. The penetrating area of the mouthpiece has a hose attached to it, which is bent by the inner contour of the pipe section. The second end of the pipe section is open, therefore the therapeutic device can be used for inhalation and exhalation. The ending of the hose section causes the device to undergo oscillatory vibration during inhalation and exhalation, thereby causing vibrations to be generated in the pharyngeal and pulmonary areas of the patient, thus allowing diseases of the airways to be treated.

Although the therapeutic device disclosed in EP 0681853 A1 has proven effective in practice, it has become apparent that no optimum treatment successes can be achieved when the air is inhaled through the hose section because the vibrations generated by the hose section during inhalation are significantly smaller in amplitude and frequency than those during exhalation.

A further disadvantage with this therapeutic device during inhalation is that the cross-sectional area of the hose section is often narrowed to such an extent that the air resistance is considerable or the hose section is completely closed, with the effect that no air can get into the patient's airways.

SUMMARY OF THE INVENTION

The object of the present invention is, therefore, to develop a therapeutic device of the aforementioned type in such a way that an oscillating air resistance can be generated during inhalation, thereby making it possible to clear the patient's airways of mucus and other impurities, or to allow the patient's airways to be trained in order to achieve a larger pulmonary volume for elite sports. At the same time, the therapeutic device should be easy to handle and be adjustable in response to the patient's individual medicinal requirements.

This is achieved in that a holding peg firmly connected to the pipe section can be pushed into the second end of the pipe section, in which case the holding peg penetrates the inside of the pipe section completely, or in part, and has a passage channel therein, and the holding peg is provided with a flexible hose attached to it that runs inside the pipe section, the free end of which can move freely in the area of the mouthpiece between the inner wall of the pipe section.

It is particularly advantageous for a screw to be inserted in the second end of the pipe section and which can be turned in relation to the pipe section and is supported on it, and for the screw to have a passage hole therein, with the holding peg inserted in it, such that the hose attached to the holding peg can be changed in its position within the pipe section. The pipe section is curved, with the effect that the hose is in contact with the inner wall of the pipe section at two positions, at least in the home position, so that turning the screw allows the contact surface between the inner wall of the pipe section and the hose to be changed, or results in torsion being applied to the hose. Such setting options have the advantageous effect that the air resistance is adapted to a patient, because the air drawn in through the mouthpiece initially flows through the hose and is output from it in a pulsed fashion. The adjustable positioning of the hose makes it possible to alter the bending of the hose and the resulting air resistance depends on the bending conditions of the hose, with the effect that each patient can adapt the air resistance of the hose to his or her individual medicinal requirements.

The air resistance can also be adjusted by making the length of the holding peg that penetrates into the pipe section variably adjustable, meaning that the hose runs inside the pipe section with different height positions.

Further advantageous configurations of the invention are disclosed hereinbelow.

BRIEF DESCRIPTION OF THE DRAWINGS

The drawings show sectional views of therapeutic devices configured in accordance with the present invention, the details of which are explained below. In the drawings, FIG. 5 shows a second sample embodiment of a therapeutic device with a curved pipe section, inside which a ventilation hose is disposed in the area of the mouthpiece and through which ambient air can be sucked in.

DESCRIPTION OF THE PREFERRED EMBODIMENTS

Figure 1:
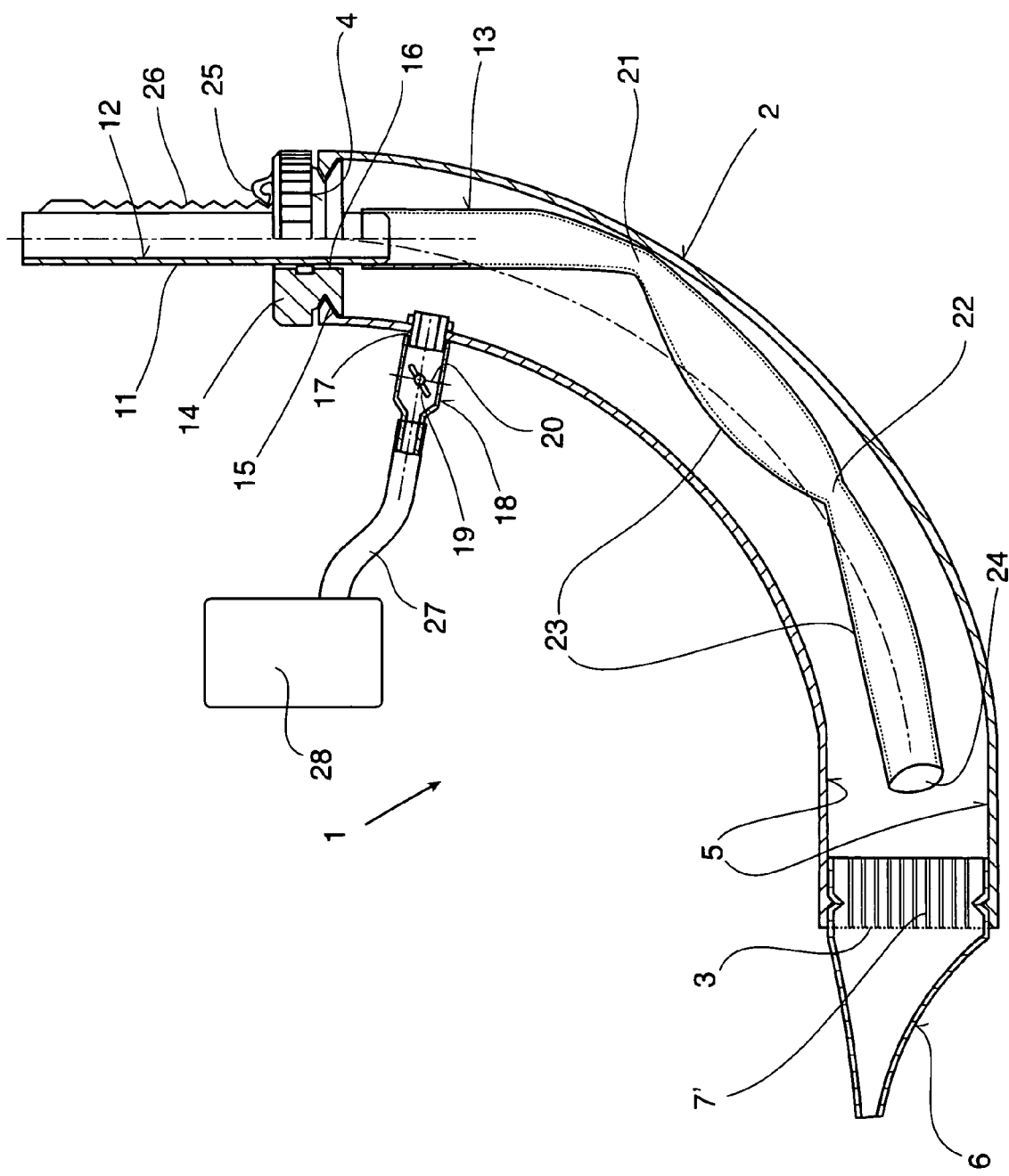
FIG. 1 shows a first illustrative embodiment of a therapeutic device with a curved pipe section, inside of which a hose attached to a holding peg makes contact, with a free end of the hose freely movable in an area of a mouthpiece between the inner walls of the pipe section, in a first operating condition.

FIGS. 1 to 4 show a therapeutic device 1 by means of which a patient's airways can be treated using an oscillating air resistance. The therapeutic device 1 in this case is used for supporting respiration during inhalation by the patient, or as a sporting implement in order to increase the pulmonary inhalation performance or a pulmonary volume of the sportsperson.

The therapeutic device 1 comprises a curved pipe section 2, the lengthways section of which is approximately that of a quarter circle. The pipe section 2 is provided with two ends 3 and 4, which are open. The first end 3 is provided with a mouthpiece 6 disposed therein, which is configured as a beak. A least one filter insert 7' or 7" is provided inside the mouthpiece 6. The filter insert 7' is arranged adjacent a free end 24 of a hose 13 and has microporous passage openings that are intended to capture impurities or other particles present in the air to be inhaled or which become detached from the hose 13. The filter insert 7" is impregnated with medicinal substrates or other substances with a therapeutic effect on the patient's airways, with the effect that air flows through the filter insert 7" during inhalation, thereby picking up particles of the medicinal substrate and transporting them into the patient's airways with every breath. FIGS. 1 to 4 show the various selection possibilities; this is because the various kinds of filter insert 7' or 7" are inserted in the mouthpiece 6.

A screw 14 is supported in a thread 15 in a rotational arrangement on the second end 4 of the pipe section 2. The centre of the screw 14 has a passage opening 16 therein, in which a holding peg 11 is disposed and is held in a height-adjustable location. The holding peg 11 therefore partially projects into the inside of the pipe section 2. The holding peg 11 fixes the position of the hose 13 fixed onto it inside the pipe section 2, with the design and configuration of the hose 13 explained in more detail below. The holding peg 11 is provided with a passage channel 12 therein which emerges in the inside of the hose 13. The ambient air is consequently sucked through the passage channel 12 into the hose 13 during inhalation, and from there into the mouthpiece 6.

A plurality of notches 26 are formed on the outside of the holding peg 11, with the notches 26 configured as undercuts. The outside of the screw 14 is provided with a detent hook 25 disposed thereon and connected to it, with the detent hook 25 engaging in a particular notch 26 so that the holding peg 11 is held on the screw 14 in a height-adjustable arrangement by the detent hook 25.

The hose 13 is provided with at least two bending areas 21 and 22 that are arranged as transitional areas between an entry area of the hose section 13 and two bulbous sub-areas 23 of the hose 13. The internal diameters of the bending areas 21 and 22 are smaller than the internal diameter of the two bulbous sub-areas 23 of the hose 13. This means turning the screw 14 enables the position of the hose 13 to be changed in relation to a wall 5 of the pipe section 2, and the hose 13 twists about its own lengthways axis. FIG. 1 shows how the bending areas 21 and 22 run in the area of the wall 5 of the pipe section 2. They can be lifted away from the wall 5 by the twisting of the screw 14. The height adjustment of the holding peg 11 enables the hose 13 running inside the pipe section 2 to be changed in its position, thereby adjusting how the hose 13 runs in relation to the wall 5 of the pipe section 2.

Figure 4:
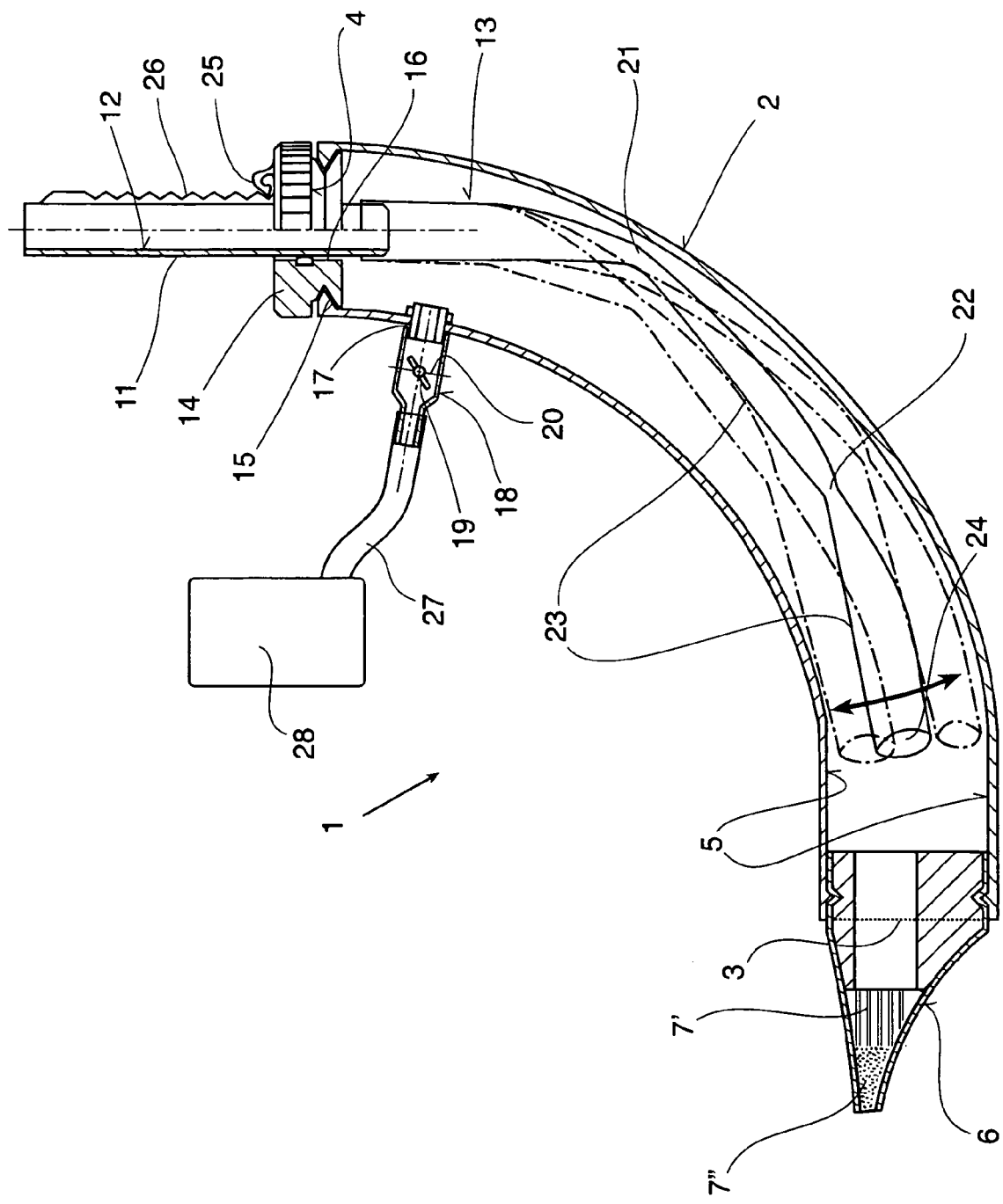
FIG. 4 shows the therapeutic device in accordance with FIG. 1 in a fourth operating condition.

During inhalation, the free end 24 of the hose 13 starts to oscillate, because it can flutter back and forth freely between the walls 5. Furthermore, individual sub-areas of the hose 13 are filled by air to different extents during the inhalation process. This is because the bending areas 21 and 22 decelerate the flow of air out of the particular sub-area 23, thereby causing the sub-area 23 on the inlet side to be inflated with a bulbous shape. FIG. 4 shows how the free end 24 of the hose 13 moves back and forth between the walls 5.

Figure 3:
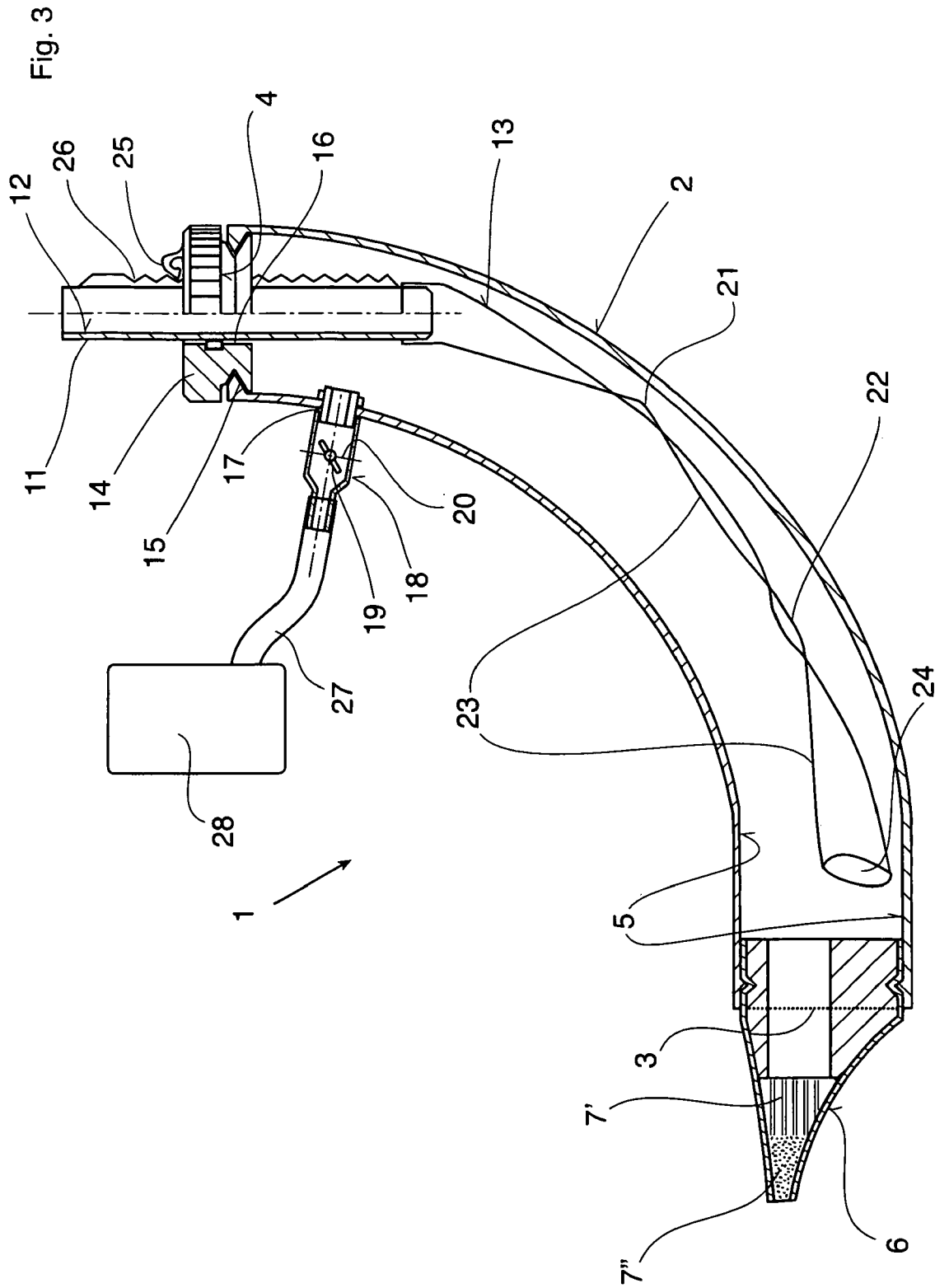
FIG. 3 shows the therapeutic device in accordance with FIG. 1 in a third operating condition.

The hose 13 in FIG. 3 has four sub-areas 23 with differently sized lengthways dimensions. The transitional areas between the bulbous sub-areas 23 are already narrowed by design measures, or the bends in the hose 13 are created by the turning of the screw 14 or by the height adjustment of the holding peg 11. A constriction of this kind in the transitional area 22 between two adjacent sub-areas 23 can also be achieved by the hose 13 making contact with the wall 5 of the pipe section 2.

Figure 2:
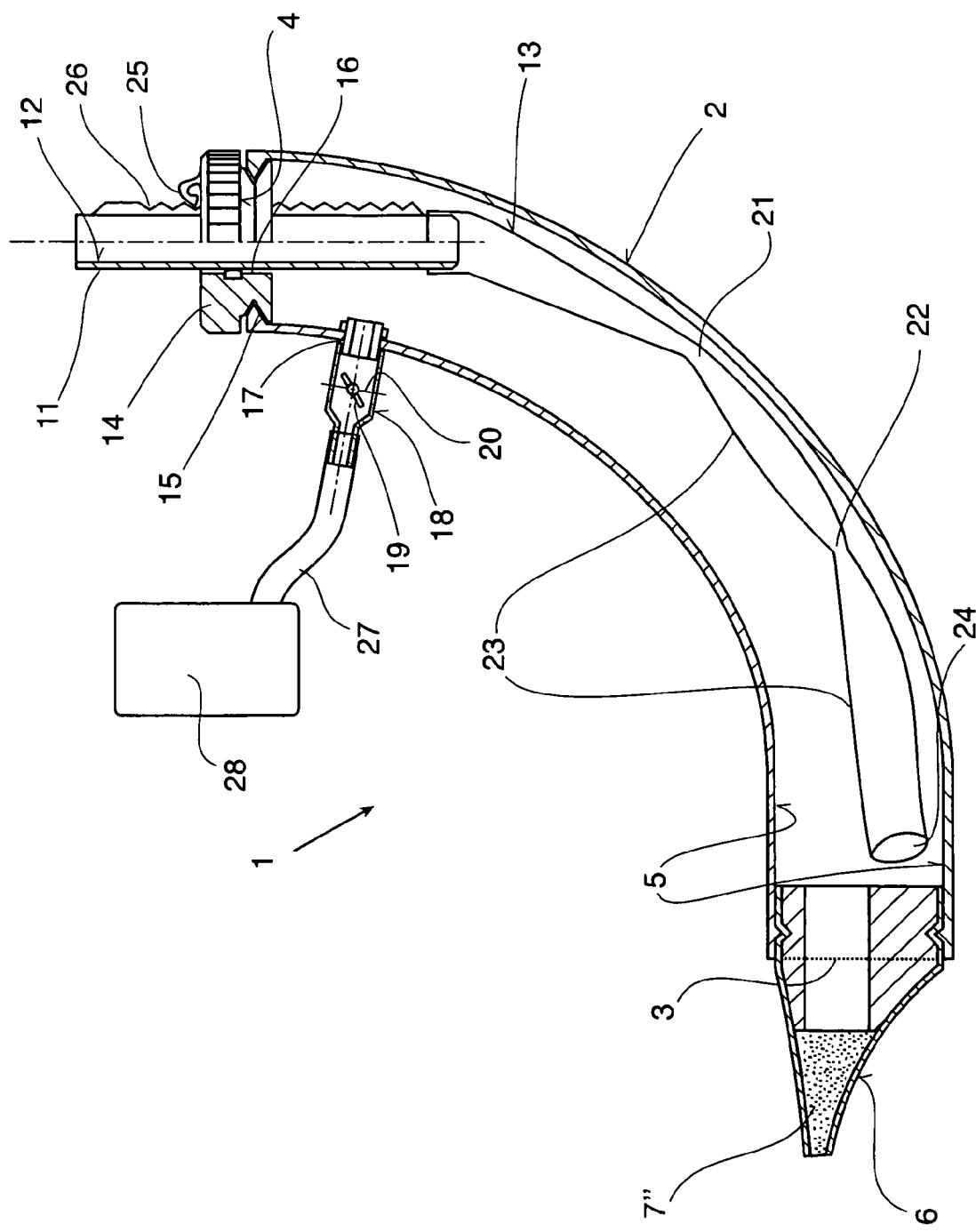
FIG. 2 shows the therapeutic device in accordance with FIG. 1 in a second operating condition.

FIG. 2 shows the holding peg 11 pushed deeper into the pipe section 2 compared to its position in FIG. 1, meaning that the hose 13 adopts a different position and therefore a different deflection compared to those in FIG. 1.

An inlet opening 17 is disposed in the wall 5 of the therapeutic device 1, with the inlet opening 17 having an inlet valve 18 pushed into it which runs in the area of the holding peg 11 and is connected to the inside of a container 28 by means of a hose 27. An adjusting element 19 changes a cross-sectional area 20 of the inlet valve 18 through which air flows, with the effect that the patient can inhale air from the atmosphere or a gas or a medicine not only through passage channel 12 and the hose 13, but also through the inlet valve 18 and its cross-sectional area through which air flows. The gas or medicine, preferably oxygen, is held in the container 28, the inside of which is connected to the inlet valve 18, and therefore enters the inside of the pipe section 2 in an adjustable quantity. The gas in the container 28 can be subjected to positive pressure or is sucked out of it by means of the patient's inhalation.

Figure 5:
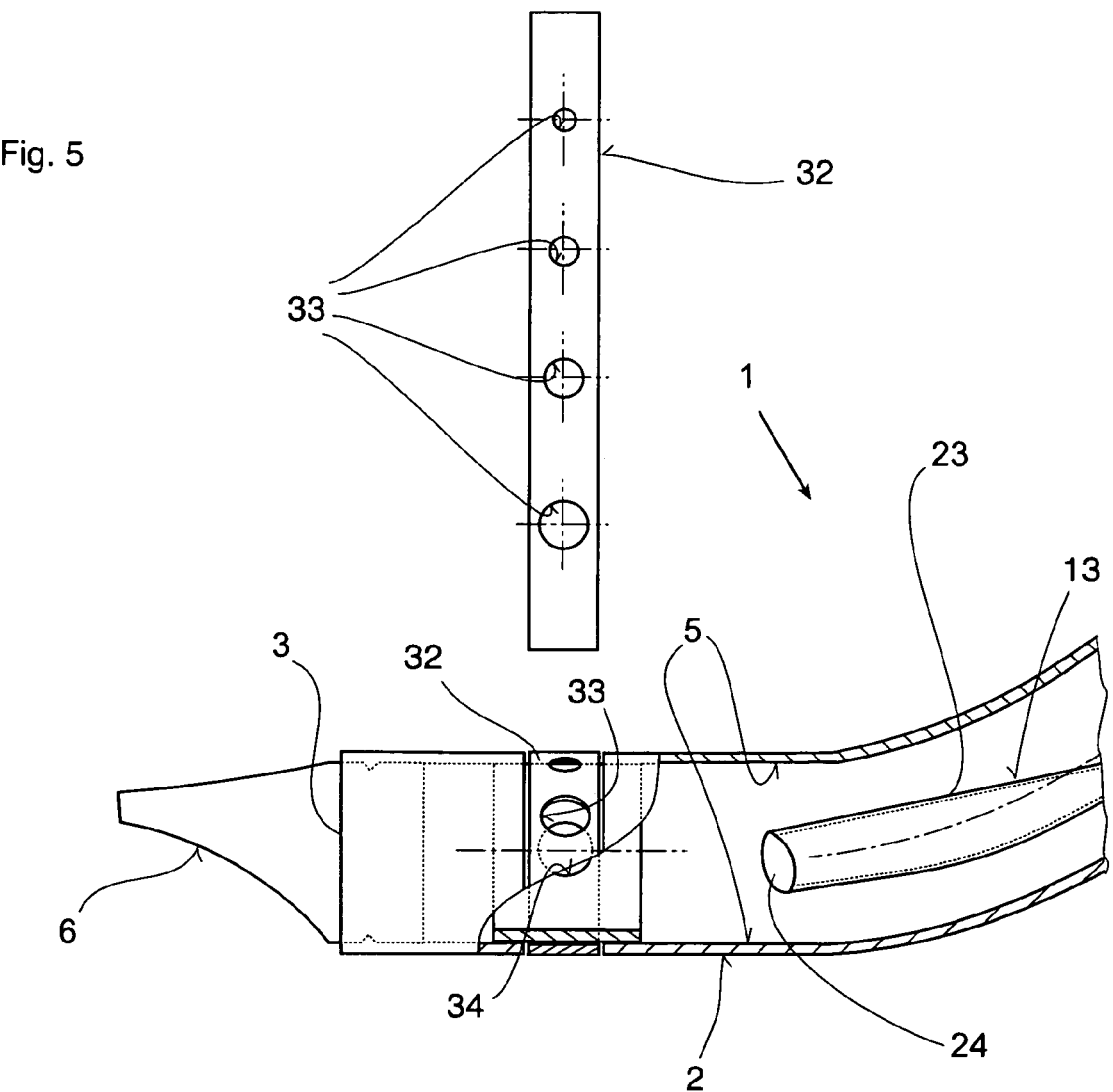
Figure 5:
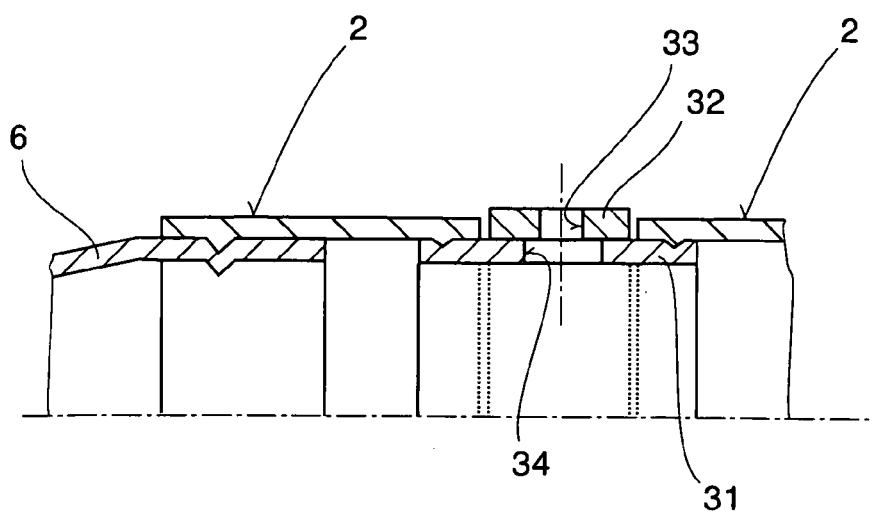

FIG. 5 shows a second sample embodiment which takes the form of a further configuration of the therapeutic device 1 according to FIGS. 1 to 4. A ventilation pipe 31 is inserted between the mouthpiece 6 and the free end 24 of the hose 13, by means of which a bypass line communicating with the atmospheric air is provided. The ventilation pipe 31 is provided with an inlet hole 34 having a specified internal diameter worked into it. The lengthways axis of the inlet hole 34 runs at right angles to the flow direction of the breathing air inside the pipe section 2. The inlet hole 34 is sealed with an adjusting ring 32 to allow the supply of ambient air through the inlet hole 34 to be adjusted. The adjusting ring 32 is mounted in a rotating arrangement on the outer circumference of the ventilation pipe 31, and four passage openings 33 are disposed in the adjusting ring 32 in the embodiment shown in FIG. 5. The four passage openings 33 have differently sized internal diameters; the largest internal diameter of the passage opening 33 in this case corresponds to the internal diameter of the inlet hole 34. If the inlet hole 34 is sealed by the adjusting ring 32, then no ambient air flows through the inlet hole 34 and the mode of function of the therapeutic device 1 corresponds to the basic version of the therapeutic device 1 in accordance with FIGS. 1 to 4.

Turning the adjusting ring 32 allows the four passage openings 33 in the adjusting ring 32 to be brought into line with the inlet hole 34, with the effect that passage opening 33 is arranged above the inlet hole 34, a specified quantity of air can be sucked into the inside of the pipe section 2 during the inhalation process. This measure achieves the effect that the patient has to exert greater pulmonary force in order to start the free end 24 of the hose 13 oscillating, because in addition to the air quantity to be sucked in through the hose 13, ambient air enters the inside of the pipe section 2 through the passage holes 33 and the inlet hole 34. In particular, it is this additional possibility for inhaling ambient air that enables a medical contribution to be made towards increasing the pulmonary volume and the pulmonary force, with the effect that the therapeutic device 1 in accordance with FIG. 5 can also be used as a sports device, for example for divers or cyclists.

Figure 6:
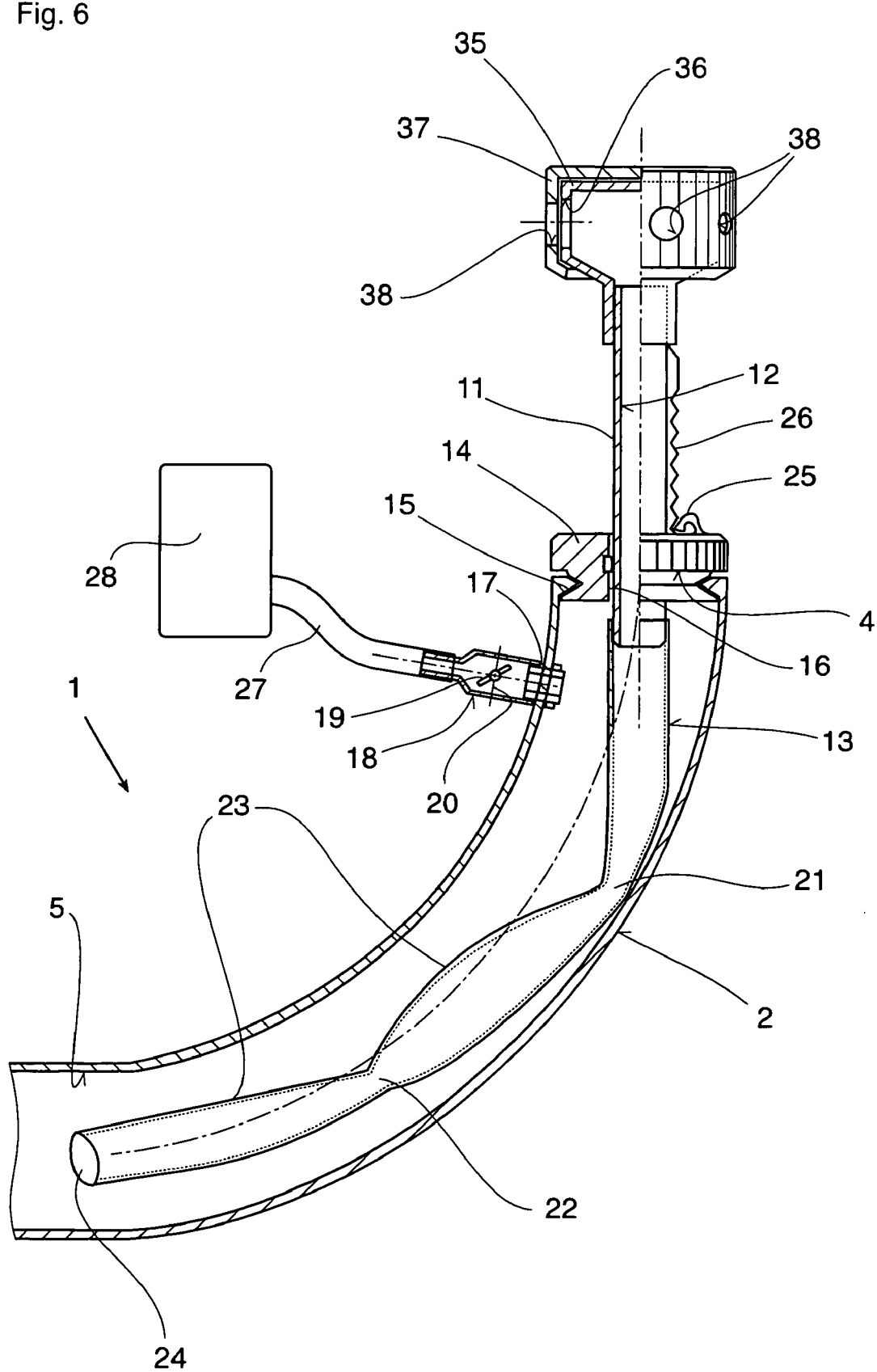
FIG. 6 shows a third sample embodiment of a therapeutic device with a curved pipe section and a holding peg inserted in it, and that has a cover providing an almost air-tight seal against the outside, by means of which the air supply can be adjusted.

FIG. 6 shows a further embodiment of the therapeutic device 1 in accordance with FIGS. 1 to 4. The free end of the holding peg 11 is sealed by a cover 35 with an inlet hole 36 therein. The inlet hole 36 is covered by an adjusting ring 37 supported on the cover 35 in a rotational arrangement. The lateral outer contour of the adjusting ring 37 has several passage channels 38 therein, the internal diameters of which differ in size in relation to one another. The largest internal diameter of the passage channels 38 in this case corresponds to the internal diameter of the inlet hole 36. This means twisting the adjusting ring 37 allows the amount of ambient air flowing through the inlet hole 36 and the corresponding passage channel 38 to be adjusted. Depending on the selected setting, it takes more pulmonary force to suck air from the atmosphere through the inlet hole 34 into the hose 13. As a result, this measure also increases the effectiveness of the therapeutic device 1 to such an extent that it can be used as a sports device for the training of elite sportspersons.

The further embodiments of the therapeutic device 1 in accordance with FIGS. 1 to 4 which are shown and explained in FIGS. 5 and 6 can be combined with one another or connected to the therapeutic device 1 in accordance with FIGS. 1 to 4 in a modular arrangement. The measures described in FIGS. 5 and 6 change the suction speed at which oscillation of the hose 13 is triggered. As a result, each patient can adjust the therapeutic device 1 in accordance with his or her personal requirements, and use it for what is referred to as incentive spirometry or as an inspirational muscle trainer. The system comprising the cover 35 and adjusting ring 37 connected to the holding peg 11, which together form a perforated ring device, adjusts and varies the inhalation pressure required when the adjusting ring 37 is turned to different positions.

What is claimed is:

1. A therapeutic device for improving the respiration of a patient, the device comprising a pipe section curved through a quarter circle and a beak-shaped mouthpiece disposed in and fully occupying of a first end of the pipe section, and a holding peg connected to a second end of said pipe section and adapted to be pushed into the second end of said pipe section, the pipe section being provided with a passage channel that extends inside said pipe section said holding peg having a flexible hose comprising at least two bulbous sub areas and at least two bending areas attached thereto that extends inside said pipe section to proximate a free end thereof, the flexible hose being movable freely in an area proximate said mouthpiece within an inner wall of said pipe section, and being bendable in at least two bending areas of the hose, wherein internal diameters of the at least two bending areas are smaller than internal diameters of the at least two bulbous sub areas.

2. The therapeutic device in accordance with claim 1, wherein a screw is disposed in the second end of said pipe section, said screw being adapted to be turned in relation to said pipe section and supported on a thread on said pipe section, wherein said screw is provided with a passage hole with said holding peg disposed in the passage hole.

3. The therapeutic device in accordance with claim 2, wherein a length of said holding peg that extends into said pipe section is adjustable by movement of said holding peg in said screw.

4. The therapeutic device in accordance with claim 2, wherein said screw is provided with a detent hook formed thereon, which engages in notches in an outside of said holding peg, and the detent hook is adapted to holds said holding peg on said screw such that said holding peg is selectively adjustable in height and extent into said pipe section.

5. The therapeutic device in accordance with claim 1, wherein an inlet opening is disposed in the wall of said pipe section, in an area proximate said holding peg, and an inlet valve is disposed in the inlet opening.

6. The therapeutic device in accordance with claim 5, wherein an adjusting element is provided in said inlet valve, by means of which a cross-sectional area of the said inlet valve through which air flows is changeable.

7. The therapeutic device in accordance with claim 5, wherein a container is connected to said inlet valve, the container containing a fluid which is adapted to flow through said inlet valve in an adjustable quantity into the inside of said pipe section by means of positive pressure and can be sucked into the pipe by means of respiration of the patient.

8. The therapeutic device in accordance with claim 1, wherein the hose when at rest makes contact with the wall of said pipe section at least at one point, and is bent by the inner contour of said pipe section.

9. The therapeutic device in accordance with claim 1, wherein the hose is provided with at least two subsections connected together by a transitional area, and an inner diameter of the transitional area is smaller in size than the inner diameters of two adjacent subsections of the hose.

10. The therapeutic device in accordance with claim 1, wherein at least one filter insert is insertable into said mouthpiece and the filter insert is adapted to cleans sucked-in air of impurities or particles, the filter insert being impregnated with a selected one of a medicine and a substrate, which is adapted to penetrate the patient's airways during inhalation.

11. The therapeutic device in accordance with claim 7, wherein a ventilation tube is disposed in said pipe section between a free end of the hose and said mouthpiece, said ventilation tube having an inlet hole with a lengthwise axis running vertical to a direction of flow of sucked-in respiratory air, and an outer surface of the ventilation tube is provided with an adjusting ring held thereon in a rotational arrangement, into which one or more passage openings with differently sized inner diameters are disposed and are flush with the inlet hole.

12. The therapeutic device in accordance with claim 1, wherein a free end of said holding peg projecting outwards is sealed with a cover (35), the cover having an inlet hole therein which is covered by an adjusting ring in a rotating mounting on the cover, and a plurality of passage channels provided in the adjusting ring and arranged flush with the inlet hole and having inner diameters of differing sizes.

\* \* \* \* \*